US00PP13281P2

(12) United States Plant Patent
Emery et al.

(10) Patent No.: US PP13,281 P2
(45) Date of Patent: Nov. 26, 2002

(54) HEUCHERA PLANT NAMED 'CANYON CHIMES'

(76) Inventors: Dara E. Emery, deceased, late of Santa Barbara, CA (US); Michael R. Lane, legal representative, 1782 Manor Dr., Vista, CA (US) 92084

( * ) Notice: Subject to any disclaimer, the term of this patent is extended or adjusted under 35 U.S.C. 154(b) by 0 days.

(21) Appl. No.: 09/203,864

(22) Filed: Dec. 2, 1998

(Under 37 CFR 1.47)

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Annette H. Para

(57) ABSTRACT

A distinct cultivar of Heuchera plant named 'Canyon Chimes', which is characterized by its compact habit and flowers with dark pink calyces and barely protruding white petals.

2 Drawing Sheets

CROSS-REFERENCE TO RELATED APPLICATIONS

The present invention is hereby cross-referenced to three related claimed inventions entitled Heuchera 'Canyon Belle' (Ser. No. 09/203,862), Heuchera 'Canyon Duet' (Ser. No. 09/203,861), and Heuchera 'Canyon Melody' (Ser. No. 09/203,863) which all four together resulted from the same breeding program as herein described.

BACKGROUND TO THE INVENTION

This new cultivar of Heuchera is the result of a long-term, controlled breeding program that was conducted by Dara Emery, Plant Breeder at the Santa Barbara Botanic Garden (SBBG), from the early 1980s until his death in 1992. 'Canyon Chimes' is a hybrid of female or seed parent Heuchera 'Canyon Delight' (unpatented) and male or pollen parent *Heuchera elegans* (unpatented).

The objective of this breeding program was to select for compact, floriferous forms of Heuchera that were more diminutive than other forms in the nursery trade. Plants that exhibited an overall dwarf stature of low-growing, mounding foliage and flowers that are similarly proportioned were selected from the various crosses made. At least one of the parents had to be a native California species, in keeping with the overall mission of SBBG's breeding program to develop garden-worthy plants from the state's native flora. In this case, *H. elegans* is the California native; it has white-pink flowers and was used for its compact size. Heuchera 'Canyon Delight' is an earlier selection bred by Mr. Emery that is an F1 hybrid of *Heuchera elegans* and a hybrid form of *Heuchera sanguinea*, the latter being an Arizonan species that is much larger in habit and used for its red flowers.

The closest comparison plants are the female or seed parent Heuchera 'Canyon Delight' and the male or pollen parent *Heuchera elegans*. 'Canyon Chimes' is distinguishable from 'Canyon Delight' by its more compact habit, smaller foliage, shorter flower stalks and flower color. 'Canyon Chimes' is distinguishable from *Heuchera elegans* by its dark pink flower color.

The cultivar was first and subsequently asexually reproduced by the inventor at the Santa Barbara Botanic Garden in Santa Barbara, Calif. by vegetative cuttings. Tip cuttings 2 to 3 inches long were put in flats of medium grade perlite and placed in a lath house mist bed with bottom heat and intermittent mist of de-ionized water. All plants so obtained exhibited identical characteristics, which were true to the original plant.

One of the parents is the variety Heuchera 'Canyon Delight' (unpatented), which was selected by the inventor at an earlier stage in the breeding program and introduced to commerce. It is referred to and described herein as a comparison variety but is not the subject of any claim.

SUMMARY OF THE INVENTION

The features that together distinguish this cultivar from other Heuchera cultivars are as follows:

1. Compact habit.
2. Dark pink flowers.

BRIEF DESCRIPTION OF THE DRAWING

The accompanying photographs depict the entire plant and a close-up of several flower stalks, illustrating the distinguishing overall habit and flower color, repectively. The illustrated and described plant is one-year-old and was grown in the nursery under 55% shade in a one-gallon container consisting of commerical pot mix of sand and composted redwood shavings at the Santa Barbara Botanic Garden in Santa Barbara, Calif. The color is as true as can be reasonably achieved by conventional photographic procedures.

Sheet 1 shows a young plant in a one-gallon container in full bloom.

Sheet 2 shows a close-up of several flower stalks, illustrating the dark pink calyces with the barely protruding white petals at the throat.

DETAILED PLANT DESCRIPTION

The following is a detailed description of the new Heuchera cultivar 'Canyon Chimes'. Observations, measurements, color determinations and comparisons were made at The Santa Barbara Botanic Garden, Santa Barbara, Calif., from two-year-old plants grown out of doors in loamy clay soil with part shade. All color values are based on the 1995 Edition of The Royal Horticultural Colour Chart, Royal Horticultural Society of London, England, except where general color terms of ordinary dictionary significance are used.

Where the variety exhibits different characteristics from the comparison commercial variety Heuchera 'Canyon Delight', the relative values or dimensions are shown in parentheses. The comparison variety has been observed under the same growing and climatic conditions as the new cultivar.

Plant orgin: Seedling from controlled breeding program.

Parentage:

*Pollen parent.*—*Heuchera elegans.*

*Seed parent.*—Heuchera 'Canyon Delight'.

Propagation: Reproduces readily the exact same characteristics from tip cuttings or division as 'Canyon Chimes'.

Rooting habit: Fibrous.

Time to develop roots: Approximately 25 days are required to form a well-developed root system.

Productivity: Produces generous number of flower stalks in spring and early summer; may rebloom again in later summer or fall with ample water.

Blooming habit: Recurrent.

Resistance to disease: We have experienced some losses of liners during unusually hot weather, possibly due to fungal pathogens in the soil.

Insects: As with most Heucheras, 'Canyon Chimes' is susceptible to mealybug infestations.

Culture: Best in part shade and loamy soil with fairly regular watering.

Growth: Medium growth rate.

Hardiness: Estimated to be Zone 6a.

Landscape value: Small-scale groundcover, edging plant, in rock gardens, or as a container specimen.

Form: Scapose perennial with many rosettes from a semi-woody erect to ascending rootstock.

Height of plant: 25 to 40 cm.

Width of plant: Approx. 25.5 cm.

Foliage:

*Leaves: in basal rosettes.*—Petioles: Color: 144A. Length: 20 to 35 mm. Texture: Pilose. Leaf Blades (5-lobed): Length: 20 to 25 mm. Width: 25 to 30 mm. Shape: broadly cordate to almost round. Margins: irregularly toothed, ciliate. Color: Varies between 137A and 137B. Texture: Upper surface: sparsely puberulent. Lower surface: glabrous.

*Inflorescence.*—Panicle, 1–2 per rosette, 20 to 30 cm long. Peduncle 8 to 16 cm long; rachis puberulent. Primary branches 8 to 11, each branch with 6 to 9 flowers.

Flower:

*Length.*—10 to 11 mm long; tubular portion of hypanthium 5 mm long.

*Buds.*—Color: 53B. Length: 4–5 mm. Width: 2 mm. Shape: pear-shaped. Hypanthium: (Externally glandular-pubescent). Color: 53D. Length: 9–11 mm (including sepals, tube and ovary). Width: 3–4 mm. Shape: Narrowly campanulate. Tube length: 7–8 mm.

*Sepals.*—Color: 53D. Number: 5. Length: 2 to 3 mm. Width: 1.5 mm. Shape: rounded to slightly acuminate. Texture: glandular. Margins: entire and glandular hairy.

*Petals.*—Color: Overall white, but faintly pink-tinged with age, color much lighter than 36D. Number: 5. Length: 4 mm inserted just below free portion of sepals. Shape: narrowly oblanceolate. Texture: glabrous. Margins: entire and glabrous.

*Stamens.*—Number: 5. Length: 4 mm. Filaments: Color: White. Shape: Linear. Anthers: Color: Between 24A and 24B. Length: 1 mm. Shape: Oval.

*Pistil.*—Length: 2.5–3 mm. Styles: Color: White. Number: 2. Length: 1.5 mm. Shape: linear.

*Ovaries.*—Position: Partly inferior. Carpels (Fused below midpoint to hypanthium): Color: 149B (free portions above attachment to hypanthium). Number: 2. Length: 3 mm.

*Fruit.*—Many seeded capsule. Color: 200D. Length: 6 mm. Width: 1.5 mm at base. Shape: Oblanceolate.

*Seed.*—Minute. Color: Black (202A). Length: 0.75 mm. Shape: Ovoid. Surface: Echinate (minutely spinose).

It is claimed:

1. A new and distinct variety of Heuchera plant named 'Canyon Chimes' as described and illustrated herein.

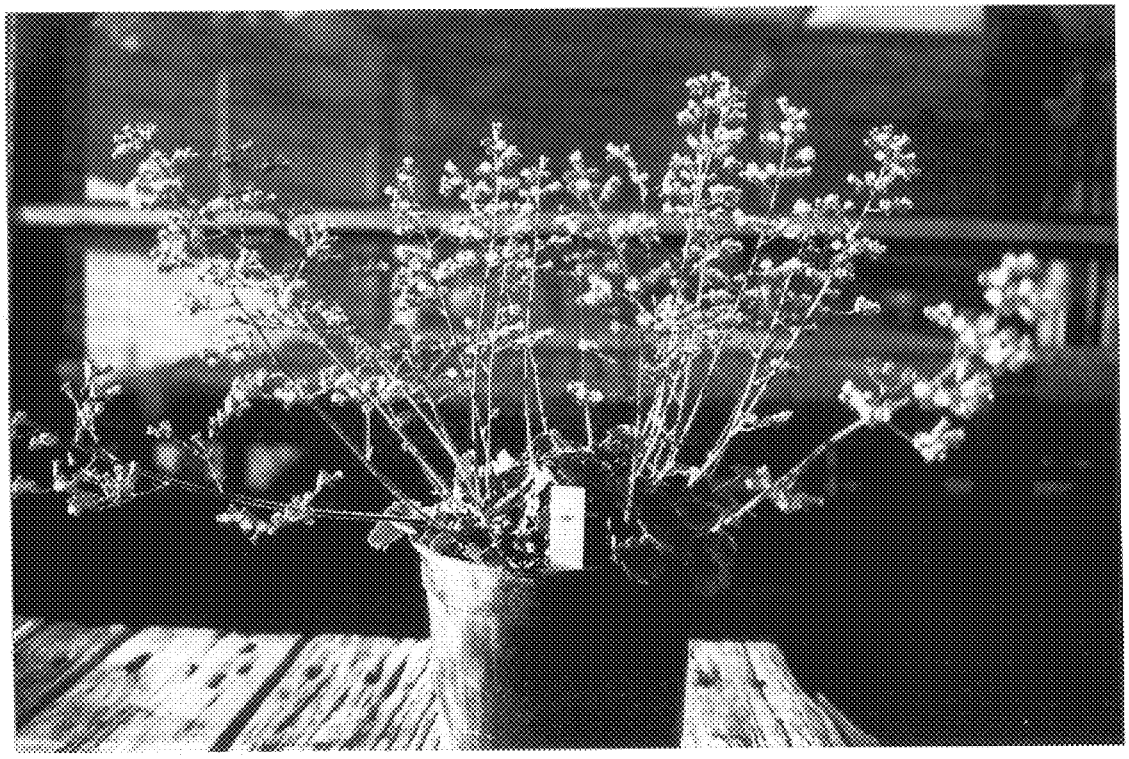

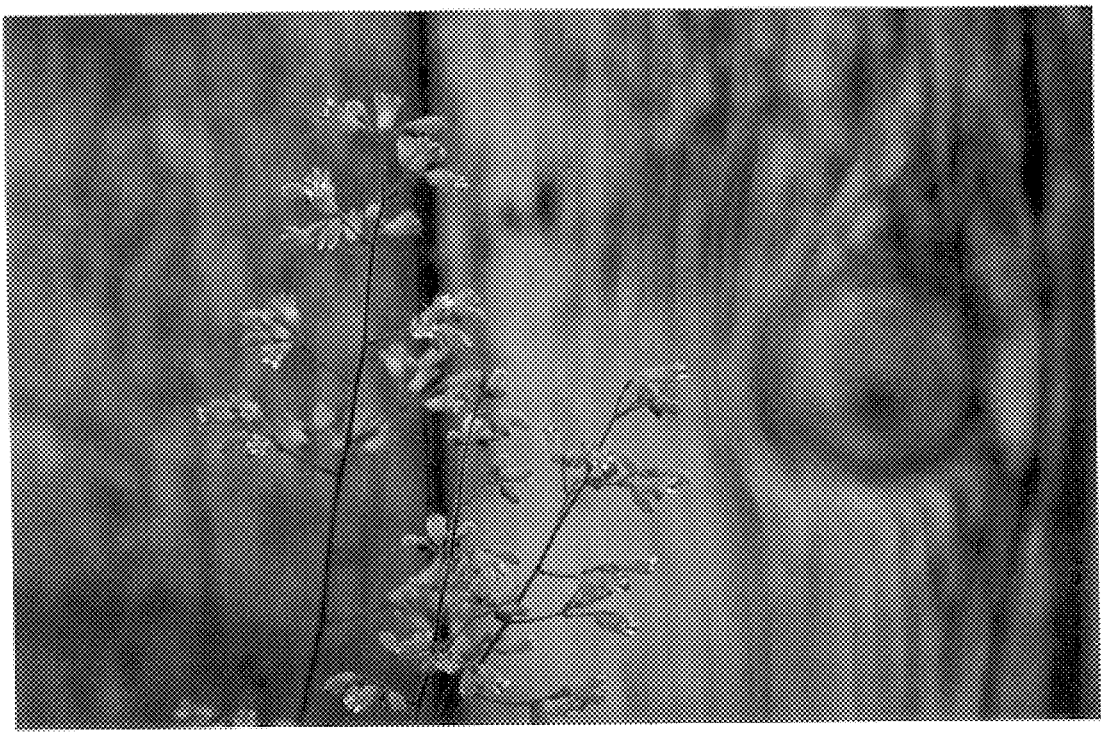

* * * * *